(12) United States Patent
Zaremba et al.

(10) Patent No.: US 7,105,487 B2
(45) Date of Patent: Sep. 12, 2006

(54) METHOD FOR INDUCING ONSET OF THE REPRODUCTIVE CYCLE OF FEMALE BREEDING ANIMALS

(75) Inventors: Wolfgang Zaremba, Homberg (DE); Uwe Hühn, Woelfershausen (DE); Armin Hess, Schwarzenborn (DE)

(73) Assignee: Veyx-Pharma GmbH, Schwarzenborn (DE)

( * ) Notice: Subject to any disclaimer, the term of this patent is extended or adjusted under 35 U.S.C. 154(b) by 0 days.

(21) Appl. No.: 10/398,842

(22) PCT Filed: Oct. 5, 2001

(86) PCT No.: PCT/DE01/03870

§ 371 (c)(1),
(2), (4) Date: Sep. 10, 2003

(87) PCT Pub. No.: WO02/28405

PCT Pub. Date: Apr. 11, 2002

(65) Prior Publication Data

US 2004/0147451 A1 Jul. 29, 2004

(30) Foreign Application Priority Data

Oct. 5, 2000 (DE) ................................. 100 50 831

(51) Int. Cl.
*A61K 38/00* (2006.01)
(52) U.S. Cl. ....................................................... 514/15
(58) Field of Classification Search .................... 514/2
See application file for complete search history.

(56) References Cited

U.S. PATENT DOCUMENTS

| | | | | |
|---|---|---|---|---|
| 3,888,838 | A | * | 6/1975 | Immer et al. ................ 530/313 |
| 4,647,553 | A | * | 3/1987 | Gulyas et al. ................. 514/15 |
| 4,753,928 | A | | 6/1988 | Gulyás et al. |
| 5,300,492 | A | * | 4/1994 | Haviv et al. .................... 514/15 |
| 5,470,847 | A | * | 11/1995 | Garfield et al. ............. 514/171 |
| 6,300,471 | B1 | * | 10/2001 | McCann et al. ............. 530/328 |

FOREIGN PATENT DOCUMENTS

| | | |
|---|---|---|
| CN | 1007318 | 3/1990 |
| HU | P9901288 | 8/1999 |
| WO | WO 9855136 A1 * | 12/1998 |

OTHER PUBLICATIONS

CAS Registry Luteinizing hormone-releasing factor (swine), RN 33515-09-2, 2004.*
1-9 Lueteinizing hormone-releasing factor (swine)—CAN RN 57773-65-6, printed Aug. 10, 2004.*
Kraeling, et al., Theriology, vol. 52, No. 9, 2000, pp. 1681-1689 (Abstract).*
Dairy Lines vol. 3, No. 3, Mar. 1997 pp. 1-3.*
Paul Pitcher, Estrus in Swine, 1997, pp. 1-2, archived Oct. 22, 1999, http://web.archive.org/web/19991012201323/cal.vet.upen.edu/swine/bio/fem/estr/hm.html.*
Sower, et al., "Primary Structure and Biological Activity of a Third Gonadotropin-Releasing Hormone from Lamprey Brain" Endocrinology, Baltimore, MD, US, Bd. 132, Nr. 3, 1993, pp. 1125-1126, and 1128-1131, XP002067663.
Yu Weh H et al., "A hypothalamic follicle-stimulating hormone-releasing decapeptide in the rat" Proc. Natl. Acad. Sci. USA, vol. 94, pp. 9499-9503, Aug. 1997 Washington, US, XP002170294.
Clark, et al., "Manipulating patterns of ovarian follicle development in cattle with progesterone and gonadotrophin releasing hormone to produce oestrous cycles with two or three follicle waves" Proceedings of the New Zealand Society of Animal Production, vol. 58, 1998, pp. 85-87, XP001145710.
Lynch, et al., "Treating cattle with progesterone as well as a GnRH analogue affects oestrous cycle length and fertility" Animal Reproduction Science, 56, 1999, pp. 189-200, XP002232439.
Sower, et al., "Primary Structure and Biological Activity of a Third Gonadotropin-Releasing Hormone FRoM Lamprey Brain" Endocrinology, Baltimore, MD, US, Bd. 132, Nr. 3, 1993, pp. 1125-1131, XP002067663.
Yu Weh H et al., "A hypothalamic follicle-stimulating hormone-releasing decapeptide in the rat" Proceedings of the National Academy of Sciences of USA, National Academy of Science. Washington, US, Bd 94, Nr. 17, 1997, pp. 9499-9503, XP002170294 (On Order).
Clark, et al., "Manipulating patterns of ovarian follicle development in cattle with progesterone and gonadotrophin releasing hormone to produce oestrous cycles with two or three follicle waves" Proceedings of the New Zealand Society of Animal Production, Bd 58, 1998, pp. 85-87, XP001145710 (On Order).
Lynch, et al., "Treating cattle with progesterone as well as a GnRH analogue affects oestrous cycle length and fertility" Animal Reproduction Science, Bd. 56, Nr. 3-4, Aug. 16, 1999, pp. 189-200, XP002232439 (On Order).
Schaefer Sabine, et al., "Synchronisation of oestrus, induction of ovulation and batch farrowing of sows" Tieraerztliche Umschau, Bd. 54, Nr. 1, Jan. 01, 1999, pp. 33-36, XP009006431 (On Order).
Pursley J R., et al., "Pregnancy rates per artificial insemination for cows and heifers inseminated at a synchronized ovulation or synchronized estrus" Journal of Dairy Science, Bd. 80, Nr. 2, 1997, pp. 295-300, XP009006475 (On Order).

(Continued)

Primary Examiner—Bruce R. Campell
Assistant Examiner—Jennifer I. Harle
(74) Attorney, Agent, or Firm—Christie, Parker & Hale LLP

(57) ABSTRACT

A method for inducing the onset of the reproductive cycle of female breeding animals is provided. To this end, the animals are injected with an agent that contains synthetically produced FSH releasing hormones as the active substance which comprise known sequences, consisting of 10 amino acids (decapeptide). The active substances are administered to the animals in the form of solution 0 to 96 hours after termination of the preceding anestrus or inhibition or a biotechnical treatment. The agents used promote an onset of the reproductive cycle after the young animals have been weaned from the mature animals and a synchronization of heat in animals that are to be inseminated for the first time.

15 Claims, No Drawings

OTHER PUBLICATIONS

Löscher W., Ungemach F. R., Kroker R., "Grundlagen der Pharmakotherapie bei Hausund Nutztieren" 1991 Verlag Paul Parey, Berlin, Hamburg, XP002232441 (On Order).

"Crystorelin details" Merial Produktinformation Cystorelin, Online, XP002232440 (On Order).

Kraeling, et al., "Luteinizing hormone response to controlled-released deslorelin in estradiol benzoate primed ovariectomized gilts" Theriogenology Jun. 2000, 53 (9):Summary only.

Naumann, et al., "Dosage reduction of d-phe-6-GnRH for the regualation of ovulation by complexation with polyglycine" Pharmazie Nov. 1991, 46(11):Summary only.

International Preliminary Examination Report of PCT/DEO1/03870, dated Jun. 25, 2005.

English Translation of International Preliminary Examination Report, with English language amended claims for International Application No. PCT/DE01/03870, International Filing Date Oct. 5, 2001.

von Sabine Schafer et al.; "Synchronization of Oestrus, Induction of Ovulation and Batch Farrowing of Sows", Tieraerztliche Umschau, vol. 54, No. 1, Jan. 1, 1999, pp. 33-38, (Abstract only) (1 pg).

Naumann, et al., "Dosage reduction of d-phe-6-GnRH for the Regulation of Ovulation by Complexation with Polyglycine" Pharmazie Nov. 1991, 46(11). (Abstract only) (1 pg).

Kraeling, et al., "Luteinizing Hormone Response to Controlled-Released Deslorelin in Estradiol Benzoate Primed Ovariectomized Gilts" Theriogenology Jun. 2000, 53 (9): (Abstract only) (1 pg).

Löscher W., Ungemach F. R., Kroker R., "Grundlagen der Pharmakotherapie bei Haus-und Nutztieren" 1991 Verlag Paul Parey, Berlin, Hamburg, (Translation of Relevant Portion) (1 pg), translation only.

Plonait et al; Lehrbuch der Schweinekrankheiten, 1988, Verlag Paul Parey, Berlin, Hamburg, pp. 266-269 (with partial English translation), translated part only.

Examination report, dated Apr. 1, 2005, for Chinese application No. 01816911.2, in the name of Veyx-Pharma GmbH.

Pursley, et al. "Pregnancy Rates Per Artificial Insemination for Cows and Heifers Inseminated at a Synchronized Ovulation or Synchronized Estrus" J Dairy Sci, 80, 1997, pp. 295-300, XP009006475.

Löscher, et al., "Grundlagen der Pharmakotherapie bei Haus-und Nutztieren" 1991, Verlag Paul Parey, Berlin, Hamburg, XP002232441 "Basis of drug therapy for domestic and production animals" Partial Translation, translation only.

"Crystorelin The trusted and effective GnRH" MERIAL Product Information, Feb. 25, 2003, XP002232440.

* cited by examiner

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: This peptide is a synthetically produced
      FSH-releasing hormone
<220> FEATURE:
<221> NAME/KEY: MISC_FEATURE
<222> LOCATION: (1)..(1)
<223> OTHER INFORMATION: The initial amino acid is pyro-glutamic acid
      (PYR or pGLU)
<220> FEATURE:
<221> NAME/KEY: MISC_FEATURE
<222> LOCATION: (10)..(10)
<223> OTHER INFORMATION: The terminal amino acid is a glycinamide
      residue (GLY-NH2)
<300> PUBLICATION INFORMATION:
<302> TITLE: Method for Inducing Onset of the Reproductive Cycle of
      Female Breeding Animals
<310> PATENT DOCUMENT NUMBER: WO 01/28405 A2
<311> PATENT FILING DATE: 2001-10-05
<312> PUBLICATION DATE: 2002-04-11
<313> RELEVANT RESIDUES: (1)..(10)

<400> SEQUENCE: 1

Glu His Trp Ser His Asp Trp Lys Pro Gly
1               5                   10
```

METHOD FOR INDUCING ONSET OF THE REPRODUCTIVE CYCLE OF FEMALE BREEDING ANIMALS

CROSS-REFERENCE TO RELATED APPLICATION

This application is a National Phase Patent Application of International Application Number PCT/DE01/03870, filed on Oct. 5, 2001, which claims priority of German Patent Application Number 100 50 831.6, filed Oct. 5, 2000.

FIELD OF THE INVENTION

The invention relates to a method for inducing the onset of the reproductive cycle of female breeding animals.

In the business and commercial sector of livestock breeding and in the production of litters, group farrowing is increasingly practiced. In conjunction with the widespread use of artificial insemination, there is the essential prerequisite of being able to supply large litters of market quality that are uniformly healthy.

At the same time, interest is increasing in suitable biotechnical methods to control the individual reproductive cycles within the combined group of animals.

The hormone systems directly involved in reproduction operate in a large regulatory cycle of neuroendocrine integration. This produces the hormonal prerequisites for the course of the heat cycle. Naturally, after the end of sexual activity, e.g., after anestrus in cyclical animals, after weaning and separation of the mothers from the young animals or after previous cycle inhibition, particularly under the influence of follicle stimulating hormones, the onset of follicle growth in the ovaries, followed by follicle ripening, onset of heat, ovulation, and possible fertilization in the event of timely insemination with a fertile sperm. The individual cycles are subject to considerable biological fluctuation. In livestock breeding, and in particular, in litter production operations with a periodic removal of farrows, there arises, for reasons of economy and animal health, interest in narrowly limited time periods for the most important reproductive events, i.e., insemination and farrowing. The targeted control of follicle growth and subsequent stages in groups of animals, e.g., weaned mature animals or gilts ready for first breeding, is used for the scheduled alignment of biological processes with necessary and desirable cycles in animal production.

Methods of cycle synchronization and influencing the reproduction functions have been developed in a variety of forms in recent years. They are based on the pharmacological possibilities of biotechnical reproduction control.

In sow management, for example, it is known to induce heat by administration of hormones. For a long time, cycle-appropriate use of gonadotropic hormone preparations of natural origin following a preceding cycle inhibition, e.g., through lactation in mature animals and heat synchronization through medication in gilts, has been considered.

The use of pregnant mare serum gonadotropin PMSG is known. PMSG is obtained from pregnant mares using the Aderlass method. Animal protection objections against this are increasing. Also, the use of certain PMSG lots, in particular those preserved in liquid form, contribute to adverse side effects, e.g., anaphylactic shock reactions.

DESCRIPTION OF THE INVENTION

The invention is directed to methods for inducing the onset of the reproductive cycle for breeding animals that is adapted to the natural biological course of the sexual cycle and causes scheduled control of the onset of follicle growth in the ovaries as well as the onset of heat in a group of breeding animals.

In an exemplary embodiment, the invention is directed to a method to induce the onset of the reproductive cycle in breeding animals, wherein an agent is used that includes as its active substance synthetically produced FSH-releasing hormones with known sequences comprising 10 amino acids (decapeptide) in addition to the usual adjuvants. The decapeptide mentioned has the amino acid sequence Pyr-His-Trp-Ser-His-Asp-Trp-Lys-Pro-Gly-$NH_2$. This sequence can be modified by the addition of further components.

It has been determined that a specific injection in animals previously in anestrus causes scheduled control of the beginning follicle growth in the ovaries. This produces, as onset of the reproductive cycle, the prerequisite for synchronization of follicle ripening, secretion of the heat hormone and the start of estrus in the treated animals. The effect is based both on the stimulation of functions of the anterior lobe of the pituitary gland as well as the ovaries, whereby a number of oocytes from the latent pool of the follicle population within or in excess of physiological limits simultaneously enter the growth phase. This effect is used for the subsequent breeding, primarily artificial insemination.

In the method according to the invention, quantities from about 5 µg to about 500 µg active substance per milliliter of injection solution are used. Preferably, the active substance quantities are from about 50 to about 300 µg and, more preferably, about 100 to about 200 µg per milliliter of injection liquid.

A suitable use variant comprises aqueous solutions that may contain further customary adjuvants in addition to the active substance.

Per animal, quantities of about 20 to about 500 µg, preferably about 50 to about 300 µg, and, more preferably, about 100 to about 200 µg of active substances are administered to each animal with each injection.

The administration of the injection solution takes place in a period of 0 to 96 hours, preferably 12 to 48 hours, and, more particularly, 24 hours after the end of a previous anestrous or cycle inhibition or a biotechnical pretreatment.

Appropriate administrations of the agent in the method according to the invention and its modifications in breeding animals are possible by means of implanted osmotic pumps, by multiple injection, as a sustained-release preparation or as an infusion with sustained-release action. Use as a sustained-release preparation yields the advantage that with one-time administration of the preparation the quantity of active substance for the triggering of the desired onset of the reproductive cycle was administered to the animals. This contributes significantly to stress reduction With the method according to the invention, a practical method to induce the onset of the reproductive cycle in breeding animals managed in groups is available. Advantageous results have been obtained in breeding sows managed in groups.

The invention is illustrated in detail in the following exemplary embodiment.

After the end of a four-week lactation, farrows were separated from breeding sows. 24 hours after separation, an injection solution that contains 125 µg active substance is administered per animal to the breeding sows to induce the onset of the reproductive cycle.

If receptivity-based insemination is planned, a verification of estrus induced by the stimulated follicles and their estrogen production is carried out. One to three inseminations are performed per estrus.

If time-based insemination is planned, an ovulation-triggering injection with an injection solution that contains D-Phe $^6$-Gonadorelin as active substance takes place at an interval of 72 hours after the injection that stimulates follicle growth.

The insemination takes place according to schedule. The first insemination is performed 24 to 26 hours after the ovulation-triggering injection and the second insemination takes place no later than 18 hours thereafter.

The invention claimed is:

1. A method for inducing onset of estrous of a sow after weaning and separation of the sow from her piglets or after a previous inhibition of the estrous cycle, comprising injecting the sow with an injection solution that contains as an active substance a synthetically produced hormone comprising the decapeptide Pyr-His Trp-Ser-His-Asp-Trp-Lys-Pro-Gly-NH$_2$, whereby the decapeptide selectively releases FSH without releasing LH.

2. A method according to claim 1 wherein the decapeptide solution is modified by the addition of further components.

3. A method according to claim 1 wherein the active substance is injected 0 to 96 hours after weaning or the end of a preceding inhibition of the estrous cycle.

4. A method according to claim 1, wherein the injection solution contains from 5 to 500 μg of active substance per milliliter of injection solution.

5. A method according to claim 1, wherein the injection solution administered per sow contains from 25 to 500 μg of active substance.

6. A method according to claim 1, further comprising administering an ovulation-triggering injection comprising as an active substance D-Phe$^6$-Gonadorelin.

7. A method according to claim 1, wherein the active substance is injected 12 to 48 hours after weaning or the end of a preceding inhibition of the estrous cycle.

8. A method according to claim 1, wherein the active substance is injected 24 hours after weaning or the end of a preceding inhibition of the estrous cycle.

9. A method according to claim 1, wherein the injection solution contains from 50 to 300 μg of active substance per milliliter of injection solution.

10. A method according to claim 1, wherein the injection solution contains from 100 to 200 μg of active substance per milliliter of injection solution.

11. A method according to claim 1, wherein the total injection solution administered to the sow contains 50 to 300 μg of active substance.

12. A method according to claim 1, wherein the total injection solution administered to the sow contains 100 to 200 μg of active substance.

13. A method according to claim 6, wherein the ovulation-triggering injection is administered after the injection solution is injected.

14. A method according to claim 13, wherein the ovulation-triggering injection is administered at least 72 hours after the injection solution is injected.

15. A method according to claim 1, wherein the increase in FSH causes follicle growth and increased estrogen production, increasing the LH level and thereby causing ovulation.

* * * * *